(12) United States Patent
Gordin et al.

(10) Patent No.: US 8,945,155 B2
(45) Date of Patent: Feb. 3, 2015

(54) CLIP FOR ASSISTING SURGICAL PROCEDURES

(75) Inventors: Udi Gordin, M.P Misgav (IL); Gilad Heftman, Kibutz Ein-Gev (IL); Moran Sobol, Kibutz Gasher (IL)

(73) Assignee: Virtual Ports Ltd., M.P. Misgav (IL)

( * ) Notice: Subject to any disclaimer, the term of this patent is extended or adjusted under 35 U.S.C. 154(b) by 649 days.

(21) Appl. No.: 12/418,094

(22) Filed: Apr. 3, 2009

(65) Prior Publication Data

US 2009/0222029 A1 Sep. 3, 2009

Related U.S. Application Data

(63) Continuation-in-part of application No. PCT/IL2007/001185, filed on Sep. 25, 2007.

(60) Provisional application No. 60/848,636, filed on Oct. 3, 2006.

(51) Int. Cl.
*A61B 17/08* (2006.01)
*A61B 1/12* (2006.01)
(Continued)

(52) U.S. Cl.
CPC ............... *A61B 1/122* (2013.01); *A61B 19/34* (2013.01); *A61B 2017/00575* (2013.01)
USPC ........................................................ 606/151

(58) Field of Classification Search
USPC .................. 606/142, 143, 151–158, 205, 213, 606/215–221; 24/3.11, 509, 510, 66.8, 331, 24/334, 336, 338, 371, 499, 500, 708.3, 24/641, 502, 503, 513; 132/231, 234, 276, 132/277
See application file for complete search history.

(56) References Cited

U.S. PATENT DOCUMENTS 1,648,228 A 11/1927 Heidt
2,702,540 A 2/1955 Debeh
(Continued)

FOREIGN PATENT DOCUMENTS

EP 1648288 7/2004
WO 03/013366 A2 2/2003
(Continued)

OTHER PUBLICATIONS

International Search Report mailed Jun. 18, 2008 for PCT/IL2007/001184 filed Sep. 25, 2007.
(Continued)

*Primary Examiner* — Katherine M Shi
(74) *Attorney, Agent, or Firm* — Paul D. Bianco; Martin Fleit; Fleit Gibbons Gutman Bongini & Bianco PL

(57) ABSTRACT

The present invention provides a clip for use during surgical procedure, comprising a body, said body is characterized by a main longitudinal axis and having a distal end and a proximal end coupled together by a shaft; said shaft is adapted to reciprocally move along said main longitudinal axis of said body; said shaft is at least partially encapsulated by a sleeve-like enveloping compression spring; said proximal end comprising actuation means; said distal end comprising one movable jaw characterized by at least one open configuration and at least one closed configuration; wherein said transformation is performed by reciprocally and linearly moving said actuation means along said longitudinal axis of said clip such that (i) said shaft is linearly moved towards and away said proximal end of said body; and, (ii) said compression spring is compressed or released such that said at least one movable jaw reconfigured.

17 Claims, 16 Drawing Sheets

(51) Int. Cl.
*A61B 19/00* (2006.01)
*A61B 17/00* (2006.01)

(56) References Cited

U.S. PATENT DOCUMENTS

| | | | | |
|---|---|---|---|---|
| 2,869,278 | A | * | 1/1959 | Cook .......................... 43/42.08 |
| 3,182,373 | A | * | 5/1965 | Strand .............................. 251/7 |
| 3,326,217 | A | | 6/1967 | Kerr |
| 3,417,752 | A | * | 12/1968 | Butler .......................... 606/147 |
| 4,106,508 | A | * | 8/1978 | Berlin ........................... 606/158 |
| 4,112,951 | A | | 9/1978 | Hulka et al. |
| 4,281,646 | A | | 8/1981 | Kinoshita |
| 4,449,532 | A | | 5/1984 | Storz |
| 4,867,139 | A | | 9/1989 | Girzadas |
| 5,052,374 | A | | 10/1991 | Alvarez-Jacinto |
| 5,297,538 | A | | 3/1994 | Daniel |
| 5,312,426 | A | | 5/1994 | Segawa et al. |
| 5,313,934 | A | | 5/1994 | Wiita et al. |
| 5,351,675 | A | | 10/1994 | Brodsky |
| 5,392,766 | A | | 2/1995 | Masterson et al. |
| 5,400,767 | A | | 3/1995 | Murdoch |
| 5,407,423 | A | | 4/1995 | Yoon |
| 5,474,057 | A | | 12/1995 | Makower et al. |
| 5,549,543 | A | | 8/1996 | Kim |
| 5,569,274 | A | | 10/1996 | Rapacki et al. |
| 5,683,349 | A | | 11/1997 | Makower et al. |
| 5,683,405 | A | | 11/1997 | Yacoubian et al. |
| 5,776,147 | A | * | 7/1998 | Dolendo ....................... 606/142 |
| 5,899,853 | A | | 5/1999 | Fowler, Jr. |
| 5,910,106 | A | | 6/1999 | Morgan et al. |
| 5,944,657 | A | | 8/1999 | Djurovic |
| 6,206,827 | B1 | | 3/2001 | Chin et al. |
| 6,354,992 | B1 | | 3/2002 | Kato |
| 6,358,196 | B1 | | 3/2002 | Rayman |
| 6,494,211 | B1 | | 12/2002 | Boyd et al. |
| 6,607,475 | B2 | | 8/2003 | Doyle et al. |
| 6,814,742 | B2 | | 11/2004 | Kimura et al. |
| 7,311,660 | B2 | | 12/2007 | Gomez |
| 7,429,259 | B2 | | 9/2008 | Cadeddu et al. |
| 7,641,644 | B2 | | 1/2010 | Chang et al. |
| 7,854,728 | B2 | | 12/2010 | Boyle, Jr. |
| 8,075,481 | B2 | | 12/2011 | Park et al. |
| 8,397,335 | B2 | | 3/2013 | Gordin |
| 2002/0022762 | A1 | | 2/2002 | Beane et al. |
| 2003/0009080 | A1 | | 1/2003 | Peng et al. |
| 2004/0024291 | A1 | | 2/2004 | Zinkel |
| 2005/0171493 | A1 | | 8/2005 | Nicholls |
| 2005/0192599 | A1 | * | 9/2005 | Demarais ...................... 606/151 |
| 2005/0251183 | A1 | * | 11/2005 | Buckman et al. .............. 606/157 |
| 2005/0283137 | A1 | | 12/2005 | Doyle et al. |
| 2006/0149135 | A1 | | 7/2006 | Paz |
| 2008/0064927 | A1 | | 3/2008 | Larkin et al. |
| 2008/0269779 | A1 | | 10/2008 | Cadeddu et al. |
| 2009/0209947 | A1 | | 8/2009 | Gordin et al. |
| 2009/0222029 | A1 | | 9/2009 | Gordin et al. |
| 2009/0250081 | A1 | | 10/2009 | Gordin et al. |
| 2010/0174150 | A1 | | 7/2010 | Park et al. |
| 2011/0124962 | A1 | | 5/2011 | Gordin |

FOREIGN PATENT DOCUMENTS

| | | |
|---|---|---|
| WO | 2005/002415 A2 | 1/2005 |
| WO | 2008/041225 A2 | 4/2008 |
| WO | 2008/041226 A2 | 4/2008 |
| WO | 2008/041227 A2 | 4/2008 |

OTHER PUBLICATIONS

Written Opinion mailed Jun. 18, 2008 for PCT/IL2007/001184 filed Sep. 25, 2007.
International Search Report mailed Sep. 9, 2008 for PCT/IL2007/001185 filed Sep. 25, 2007.
Written Opinion mailed Sep. 9, 2008 for PCT/IL2007/001185 filed Sep. 25, 2007.
International Search Report mailed Mar. 10, 2009 for PCT/IL2007/001186 filed Sep. 25, 2007.
Written Opinion mailed Mar. 10, 2009 for PCT/IL2007/001186 filed Sep. 25, 2007.
International Preliminary Report on Patentability issued Aug. 4, 2009 for PCT/IL2007/001186 filed Sep. 25, 2007.
International Preliminary Report on Patentability issued Apr. 7, 2009 for PCT/IL2007/001185 filed Sep. 25, 2007.
International Preliminary Report on Patentability issued Apr. 7, 2009 for PCT/IL2007/001184 filed Sep. 25, 2007.
International Search Report published Dec. 10, 2009 for PCT/IL2009/00550 filed Jun. 2, 2009.
Written Opinion of the International Searching Authority mailed Sep. 29, 2009 for PCT/IL2009/00550 filed Jun. 2, 2009.
International Preliminary Report on Patentability published Dec. 6, 2010 for PCT/IL2009/00550 filed Jun. 2, 2009.
U.S. Appl. No. 60/848,636, filed Oct. 3, 2006.
Restriction Requirement mailed Nov. 1, 2011 for U.S. Appl. No. 12/418,030, filed Apr. 3, 2009.
Response to Restriction Requirement mailed Nov. 1, 2011 for U.S. Appl. No. 12/418,030, filed Apr. 3, 2009 filed Dec. 1, 2011.
Office action dated Nov. 1, 2012 for U.S. Appl. No. 12/995,825.
Response to office action filed May 26, 2012 for U.S. Appl. No. 12/418,030.
Office Action for U.S. Appl. No. 12/418,128 dated Jun. 12, 2012.
For U.S. Appl. No. 12/418,030: Notice of allowance dated Nov. 13, 2012; amendment filed Sep. 26, 2012; notice re non-compliant amendment dated Aug. 24, 2012, Amendment dated Jul. 23, 2012; notice re noncompliant amendment Jun. 29, 2012.
Office Action issued Jan. 26, 2012 for U.S. Appl. No. 12/418,030, filed Apr. 3, 2009.
For U.S. Appl. No. 12/995,825 response to USPTO office action, dated Mar. 29, 2013.
Supplemental Response dated Jul. 30, 2014 for U.S. Appl. No. 12/995,825.
Supplemental Response dated Jul. 29, 2014 for U.S. Appl. No. 12/995,825.
Office action dated Apr. 29. 2014 for U.S. Appl. No. 12/995,825.

* cited by examiner

CLIP FOR ASSISTING SURGICAL PROCEDURES

CROSS REFERENCE TO RELATED APPLICATIONS

This application is a continuation-in-part application of International Application No. PCT/IL2007/001185, filed 25 Sep. 2007, which claims priority to U.S. Provisional Application No. 60/848,636, filed Oct. 3, 2006. The entire contents of each of these applications are incorporated herein by reference.

FIELD OF THE INVENTION

The present invention generally relates to a clip device, system and method for assisting surgical procedures. More specifically the present invention is related to minimally invasive surgery, including but not limited to: endoscopic surgery, laparoscopic surgery and Natural Orifice Transluminal Endoscopic Surgery (NOTES)

BACKGROUND OF THE INVENTION

Endoscopic surgery interventions represent a significant advance in various fields of surgery permitting the performance of the majority of interventions through a number of small incisions reducing postoperative pain and enhancing postoperative recovery.

In endoscopic surgery, the surgeon performs the operation through small holes using long instruments and observing the internal anatomy with an endoscope camera.

However there are still a significant number of drawbacks to this technique. The fixed position of the access openings in the wall of the cavity access-ports significantly limits the approach to some surgical locations making some interventions very long and technically demanding. Creation of additional ports may negate the minimal invasive nature of the procedure. Some ports are used mainly for introducing retracting instruments in order to better access to the exact surgery location.

The fixed position of the ports may hinder retraction in various directions, and the limited potential access sites (as for example anterior and lateral walls, but not posterior, proximal and distal walls of the abdomen for abdominal laparoscopy) may make retraction in some directions impossible.

This invention relates to anchoring devices for retractors, being attached to the internal surface of a cavity or to various organs within a cavity, during minimally invasive surgery.

Magnetic attraction has been used in medicine to remotely attach devices to tissue, or to remotely manipulate tissue. So, in U.S. Pat. No. 6,358,196, issued to RAYMAN REIZA magnetic substances are introduced into the intestine by ingestion and the intestines are remotely manipulated by an electromagnet during laparoscopic surgery. However this device does not permit retraction of an abdominal organ other than intestine and does not permit precise retraction of a particular segment of intestine. Also it should be pointed out that the magnets might have impact on other metal instruments during operations and has limited options for obese patients where tissues thickness requires extremely strong magnets. The present invention, on the contrary, provides a clip for general use in surgeries in addition to internal retraction.

In U.S. patent application 2003/009080 and in U.S. Pat. No. 6,494,211, a suction device is used to attach a retractor to various organs such as the heart in order to retract it in a specific direction. However these devices are introduced trough orifices in the body wall and they are not virtual ports since they can not permit non invasive anchoring of the retractor to the undersurface of the cavity wall, or within the cavity in another location than the access port. In other words, the device as provided by the above mentioned patent and patent application 'holds' the suction outside the body rather than self anchoring the device within the body.

In PCT No. W003013366 and in U.S. Pat. No. 6,206,827 a retractor device is attached to the organ to be retracted by some adhesive. However, the retractors are introduced through an orifice and do not represent a virtual port since they can not permit non invasive anchoring of the retractor to the undersurface of the cavity wall, or within the cavity in another location than the access port. Again, as described above, the above mentioned patent requires outside grabbing of the device.

In U.S. Pat. No. 6,206,827, a retractor is directly attached to tissue by penetrating it with mechanical sharp means such as barbs or springs and traction on this means cause tissue retraction. However, the retractors are introduced through an orifice and do not represent a virtual port since they can not permit non invasive anchoring of the retractor to the undersurface of the cavity wall, or within the cavity in another location than the access port. Again, as described above, the above mentioned patent requires outside grabbing of the device.

Thus, there is a long felt need for a better anchoring device that permits anchoring of the retractor to the undersurface of the cavity wall without adding additional significant incisions to the abdominal wall For a self anchoring device there is a need for a device diameter which will fit standard trocars, such as 5 mm diameter, and obtaining such clip with which the desired force could be exerted is very challenging.

The present invention presents a mechanical implementation of such clip, system and method for use this clip for retraction of internal organs during minimally invasive surgery.

SUMMARY OF THE INVENTION

It is one object of the invention to disclose a clip for use during surgical procedure; wherein said clip is provided with a sleeve-like enveloping compression spring; further wherein said compression spring surrounds the jaws of said clip and constrains said jaws to be close to each other.

It is another object of the invention to disclose the clip as defined above, wherein said clip is provided with a hook or loop engagement means for engagement with an introducer.

It is another object of the invention to disclose the clip as defined above, wherein said engagement hook is adapted to provide anchoring to walls within the abdominal cavity and/or within a hollow body organs and/or natural/artificial orifices and/or spaces and/or post operative spaces.

It is another object of the invention to disclose the clip as defined above, wherein said clip is actuated by pulling on the engagement means, while counter-force is exercised on the base of the tool.

It is another object of the invention to disclose the clip as defined above, wherein said engagement means open the jaws of said clip.

It is a further object of the invention to disclose the clip as defined in any of the above, wherein the transformation of the clip from the open configuration to the closed configuration or from the closed configuration to the open configuration occurs without any plastic deformation of sad at least one movable jaw.

It is a further object of the invention to disclose the use of the clip as defined in any of the above for in performing an operation selected from the group consisting of anchoring minimally invasive surgical devices during said surgical procedures, retracting internal organs, retracting tissue within said body cavity, and temporarily holding a blood vessel.

It is another object of the invention to disclose a system for use during surgical procedure. The system comprising: (a) at least one clip as defined above; (b) at least one introducer.

It is another object of the invention to disclose the system as defined above, wherein said clip is provided with a hook or loop engagement means for engagement with an introducer.

It is another object of the invention to disclose the system as defined above, wherein said engagement hook is adapted to provide anchoring to walls within the abdominal cavity and/or within a hollow body organs and/or natural/artificial orifices and/or spaces and/or post operative spaces.

It is another object of the invention to disclose the system as defined above, wherein said introducer is adapted to introduce said clip into the abdominal cavity and/or into a hollow body organs and/or natural/artificial orifices and/or spaces and/or post operative spaces.

It is another object of the invention to disclose the system as defined above, wherein said introducer is adapted to be disconnects said clip from within the abdominal cavity and/or within a hollow body organs and/or natural/artificial orifices and/or spaces and/or post operative spaces.

It is another object of the invention to disclose the system as defined above, wherein said clip is adapted to be actuated by pulling said engagement means by said introducer, while counter-force is exercised on the base of the clip.

It is another object of the invention to disclose the system as defined above, wherein said introducer is adapted to reconnect said clip within the abdominal cavity and/or within a hollow body organs and/or natural/artificial orifices and/or spaces and/or post operative spaces.

It is another object of the invention to disclose the system as defined above, wherein said introducer is adapted to extract said clip from the abdominal cavity and/or from a hollow body organs and/or natural/artificial orifices and/or spaces and/or post operative spaces.

It is another object of the invention to disclose the clip as defined above, used for anchoring devices and/or interchangeable tips during surgical procedures and/or retracting internal organs and/or tissue inside the abdominal cavity and/or inside a hollow body organs and/or natural/artificial orifices and/or spaces and/or post operative spaces.

It is another object of the invention to disclose the system as defined above, additionally comprising anchoring devices.

It is another object of the invention to disclose the system as defined above, wherein said anchoring devices comprising: connected first and second attaching means, said first attaching means for attaching the device to an internal surface within a cavity of the human body and said second attaching means for attaching to surgical instruments or devices within said cavity.

It is another object of the invention to disclose the system as defined above, wherein said first attaching means comprises minimally invasive means for attaching to the internal surface of a cavity or to various organs within a cavity, said means are selected from vacuum means, such as vacuum cups; magnetic means, such as magnets or electromagnets situated on either interior, exterior or both surfaces of the cavity; mechanical means, especially barbs, fixation wires or self retaining clamps; adhesive means, especially pressure adhesive gel or any combination thereof.

It is another object of the invention to disclose the system as defined above, additionally comprising means allowing it to be moved from one position to another and to be reattached to the under surface of the cavity, or to various tissues within a cavity, without creating any additional significant openings in the cavity wall.

It is another object of the invention to disclose the system as defined above, additionally comprising means for attaching a plurality of anchoring devices, selected from vacuum cups, magnetic means, mechanical means, adhesive means or any combination thereof, used together for holding a larger weight or for distributing the load therebetween.

It is another object of the invention to disclose the system as defined above, wherein said second attaching means is selected from a group comprising mechanical means, such as a vacuum cup, a hook and loop attachment, a connecting string or a rod; adhesive means, magnetic means or any combination thereof, further wherein said surgical devices attached to said second attaching means is selected from a group comprising: cutting means; blood sealing units; illumination means; imaging means, such as a camera and camera cleaning means; or a minimally invasive forcing means by which force is exerted upon the cavity walls or upon various organs within the cavity, especially a pulling means, such as wires for attaching to another internal surface of the cavity or to various organs within the cavity; a pushing means, such as rods for attaching to another internal surface of the cavity or to various organs within the cavity; or any combination thereof.

It is another object of the invention to disclose a method for retraction of an internal organ during a surgical procedure. The method comprises steps selected inter alia from (a) obtaining a system as defined above; (b) introducing said clip into the abdomen cavity and/or into a hollow body organs and/or natural/artificial orifices and/or spaces and/or post operative spaces; (c) opening said clip's jaws via said introducer; (d) grabbing an internal organ or tissue via said jaws; (e) anchoring said clip's hook to the internal wall of said abdominal cavity and/or said hollow body organ and/or said natural/artificial orifices and/or said spaces and/or said post operative spaces; (f) disconnecting said introducer from said clip; and (g) removing said introducer from said abdominal cavity and/or said hollow body organs and/or said natural/artificial orifices and/or said spaces and/or said post operative spaces. Thereby the need of additional incisions to said abdominal wall is avoided.

It is another object of the invention to disclose the method as defined above, additionally comprising the step of reconnecting said clip within said abdominal cavity and/or said hollow body organs and/or said natural/artificial orifices and/or said spaces and/or said post operative spaces via said introducer.

It is another object of the invention to disclose the method as defined above, additionally comprising the step of repositioning the clip and/or removing the clip from said abdominal cavity and/or said hollow body organs and/or said natural/artificial orifices and/or said spaces and/or said post operative spaces.

BRIEF DESCRIPTION OF THE FIGURES

In order to understand the invention and to see how it may be implemented in practice, and by way of non-limiting example only, with reference to the accompanying drawing, in which.

DETAILED DESCRIPTION OF PREFERRED EMBODIMENTS

Figure 1:
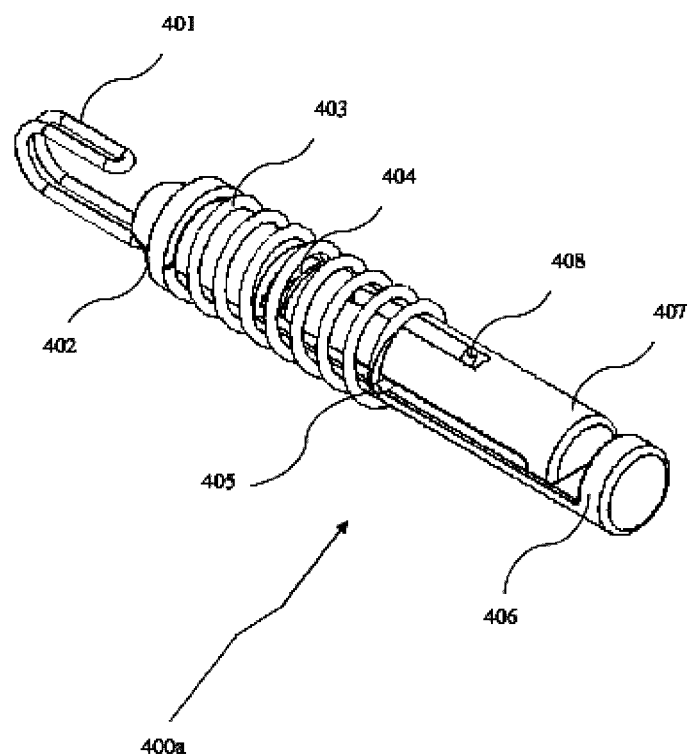
FIG. 1 is a perspective view of a clip according to another embodiment of the present invention, in its closed configuration.

The following description is provided, alongside all chapters of the present invention, so as to enable any person skilled in the art to make use of the invention and sets forth the best modes contemplated by the inventor of carrying out this invention. Various modifications, however, will remain apparent to those skilled in the art, since the generic principles of the present invention have been defined specifically to provide anchoring devices attached to undersurface of a cavity surface for assisting laparoscopic procedures.

U.S. application Ser. No. 10/563,229, PCT publication no. WO2005/002415, and EP Application No 04 744 933.5 are incorporated in all its parts as a reference to the current invention. Exemplary descriptions and embodiments of the anchoring of the clip are found in U.S. application Ser. No. 10/563,229, PCT publication no. WO2005/002415, and EP Application No. 04 744 933.5.

The present invention provides a clip for use during surgical procedure. The clip is provided with a sleeve-like enveloping compression spring. The compression spring surrounds at least a part of the jaws of said clip and constrains said jaws to be close to each other. In other embodiments the compression spring does not surround the jaws.

The present invention also provides a system for use during surgical procedure. The system comprising: (a) at least one clip; and (b) at least one introducer.

The present invention also provides a method for retraction of an internal organ during a surgical procedure. The method comprises steps selected inter alia from:
(a) obtaining a system; (b) introducing the clip into the abdomen cavity and/or into a hollow body organs and/or natural/artificial orifices and/or spaces and/or post operative spaces;
(c) opening the clip's jaws via the introducer;
(d) grabbing an internal organ or tissue via the jaws; (e) anchoring the clip's hook to the internal wall of the abdominal cavity and/or a hollow body organ and/or natural/artificial orifices and/or spaces and/or post operative spaces;
(f) disconnecting the introducer from the clip; and, (g) removing the introducer from the abdominal cavity and/or hollow body organs and/or natural/artificial orifices and/or spaces and/or post operative spaces. Thereby the need of additional incisions to said abdominal wall is avoided.

The term "introducer" refers hereinafter to any surgical instrument specially designed for providing access during a surgery or operation.

The term "endoscopic surgery" refers hereinafter to procedures performed inside the body through small incisions or within the lumen of an organ with the aid of a special camera.

The term "endoscopic instruments" refers hereinafter to surgical instruments or devices using during endoscopic surgery.

The term "minimally invasive surgery" refers hereinafter to a procedure that is carried out by entering the body through the skin or through a body cavity or anatomical opening, but with the smallest damage possible.

The term "trocar" refers hereinafter to a surgical instrument passed through the body, used to allow easy exchange of endoscopic instruments during endoscopic surgery.

The term "compression spring" refers hereinafter to a type of a spring that applies a resistive force as it is compressed.

The term 'virtual port' refers hereinafter to a surgical device introduced within a body cavity without need of dedicated incision and/or port but by using other port.

The term "body cavity" refers hereinafter to any cavity within the body such as within said abdominal cavity and/or within hollow body organs and/or within the natural/artificial orifices and/or within the spaces and/or to the post operative spaces.

Figure 2:
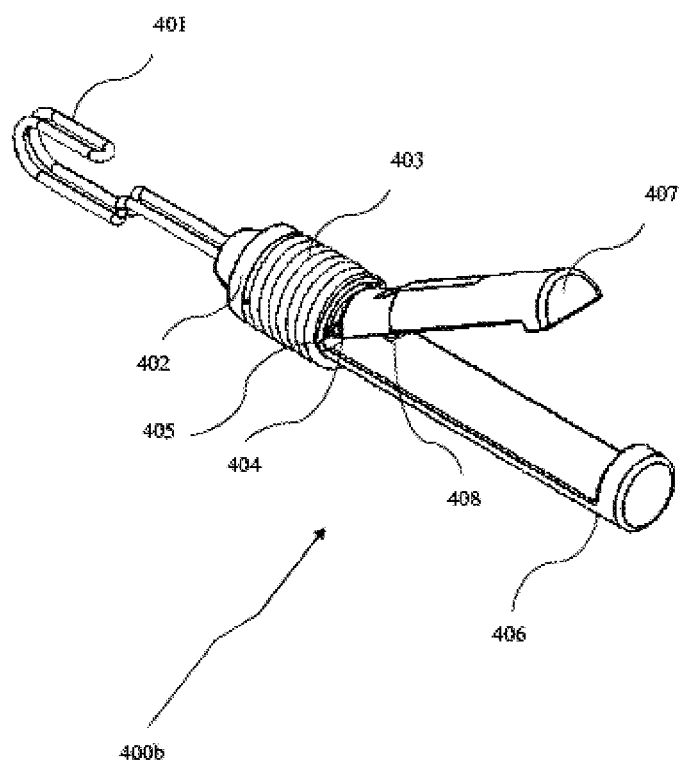
FIG. 2 is a perspective view of the same in its opened configuration.

Reference is made now to FIGS. 1 and 2 representing a clip 400(a,b) according to one embodiment of the present invention. According to that embodiment at least one jaw is movable from an open configuration to a closed configuration and at least one fixed jaw. A compression spring 403 encircles the clip base 402 and at least a portion of the movable jaw 407 as a sleeve, permitting a very simple engagement of the clip by a hook 401 and actuation (of at least one jaw) through linear movement (i.e., linear movement along the main longitudinal axis of the clip). The actuation opens at least one of the jaws (the movable one) from its closed configuration (400a) to its open configuration (400b) by rotation of the movable jaw 407 around a hinge 404 and moves away from the fixed jaw 406, as the opening means 408 is retracted proximally by pulling it to its distal end—(i.e., towards the engaging hook 401). Alternatively, both jaws can move relative to one another.

In other words, the spring 403 in its default configuration encapsulates at least a portion of the clip base (i.e., body, 402) and at least a portion of the opening means (i.e., a shaft 408).

The operation of reconfiguring said at least one jaw is as follows:

The engaging hook 401 is pulled towards the distal end of the clip. Since the engaging hook 401 is coupled to a shaft 408 (which can reciprocally and linearly move along the longitudinal axis of the clip), once the hook 401 is pulled, the shaft 408 is pulled also (relatively to the body 402).

Since the shaft comprises at least one stopping means 405 (adapted to constrains the spring's movement), the shaft's movement results in compression of the spring 403.

This compression enables the opening of the jaw.

The clip is, by default, in its closed configuration due to the compressing spring 403 fixed between the proximal end of the body of the clip 402 and the distal end of the hook 401. As the spring tends to expand to its relaxed state, it applies force on the movable jaw 407 closing it relative to fixed jaw 406 and causing force to be applied the tissue trapped between the jaws.

Figure 3:
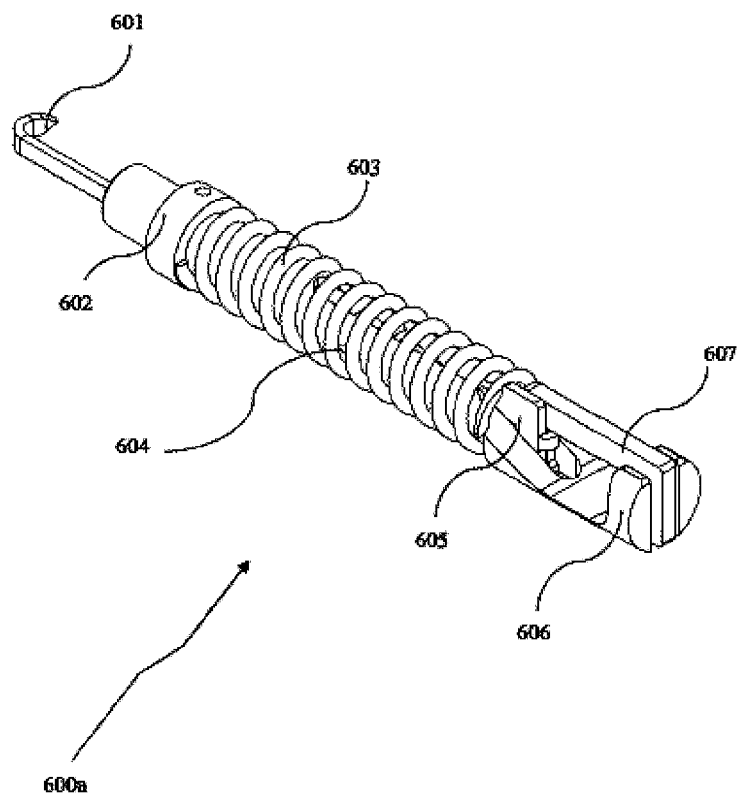
FIG. 3 is a perspective view of a clip according to yet another embodiment of the present invention, in its closed configuration.
Figure 4:
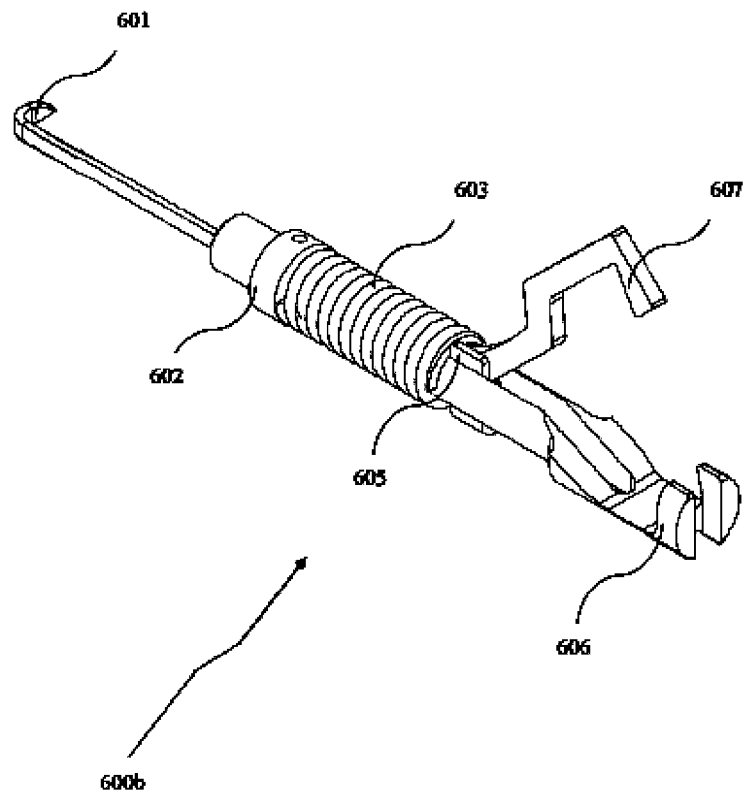
FIG. 4 is a perspective view of the same in its opened configuration.

Reference is made now to FIGS. 3 and 4 representing a clip 600(a,b) according to another embodiment of the present invention wherein a spring 603 encircles the ring on the clip base (i.e., body) 602 and movable jaw 607 as a sleeve. Much like the previous embodiment, actuation opens the clip and transforms it from its closed configuration 600a to its open configuration 600b by rotating the movable jaw 607 around hinge 604. Such actuation moves the movable jaw 607 away from the fixed jaw 606, as the opening means 605 (i.e., shaft) is retracted proximally by pulling on its proximal end—towards the engaging hook 601.

In other words, the spring 603 in its default configuration encapsulates at least a portion of the clip base (i.e., body, 602) and at least a portion of the opening means (i.e., a shaft 605).

The operation of reconfiguring said at least one jaw is as follows:

The engaging hook 601 is pulled towards the distal end of the clip. Since the engaging hook 601 is coupled to a shaft 605 (which can reciprocally and linearly move along the longitudinal axis of the clip), once the hook 601 is pulled, the shaft 605 is pulled also (relatively to the body 602).

The shaft's movement is adapted to result in compression of the spring 603, such that said compression of said spring enables the opening of the jaw.

The clip tends to be in its closed configuration, due to the compressed spring 603 fixed between the ring on end of the body of the clip 602 and the opening means distal end 605. As the spring tends to expand to its relaxed state, it applies force on the movable jaw 607 closing it relative to fixed jaw 606 and causing force to be applied the tissue trapped between the jaws.

The present invention also discloses an introducer, which is a minimally invasive device for introducing, actuating and removing clips of above mentioned embodiments during surgery within a cavity of the human body.

Figure 5:
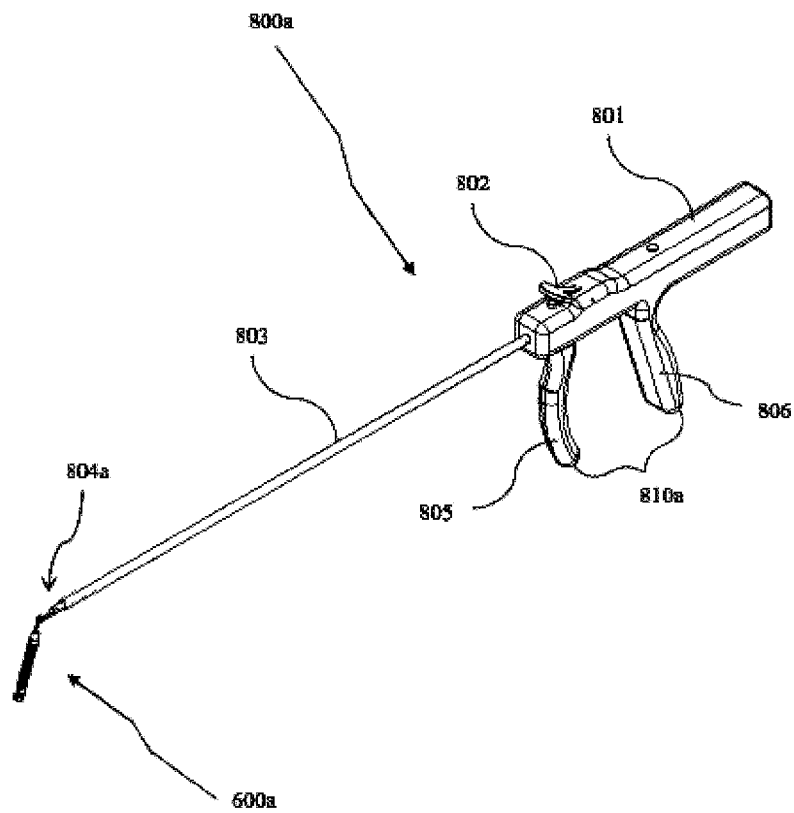
FIG. 5 is a perspective view of an introducer according to one embodiment of the present invention, engaging the clip of FIG. 6.
Figure 6:
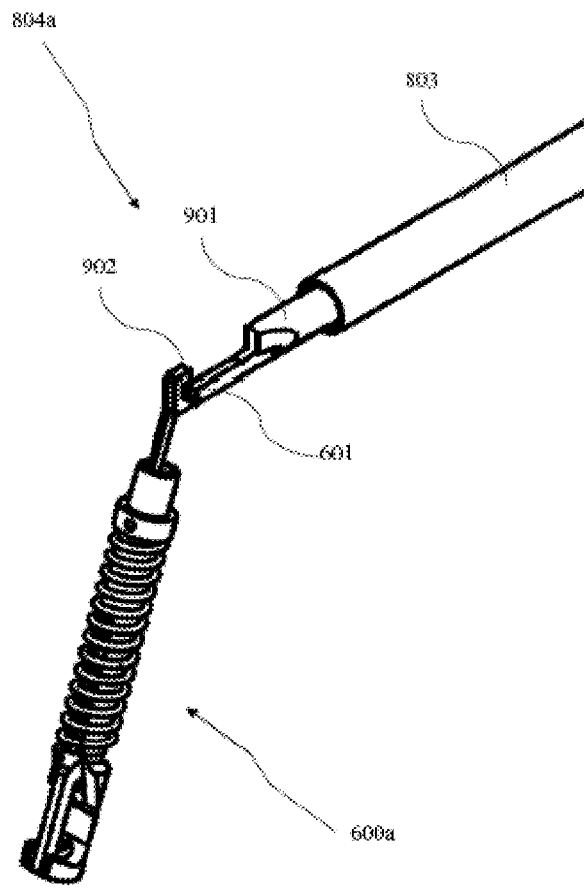
FIG. 6 is an enlarged view of FIG. 8, focused on the distal end of the introducer and the clip.
Figure 7:
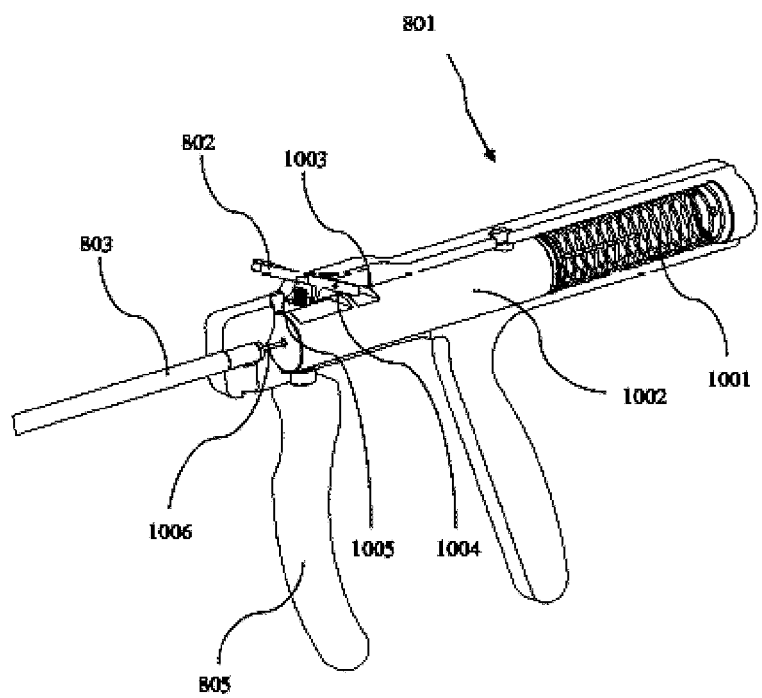
FIG. 7 is an enlarged, perspective, cross section view of the introducer, focused on the body and mechanism of the introducer.
Figure 8:
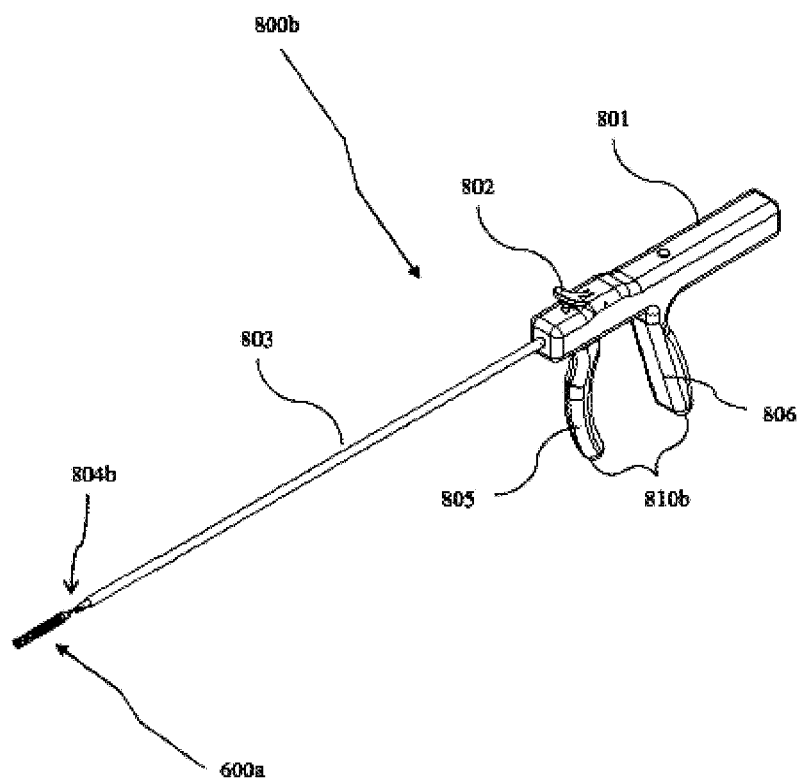
FIG. 8 is a perspective view of the introducer engaging the clip with the introducer's trigger partially contracted.
Figure 9:
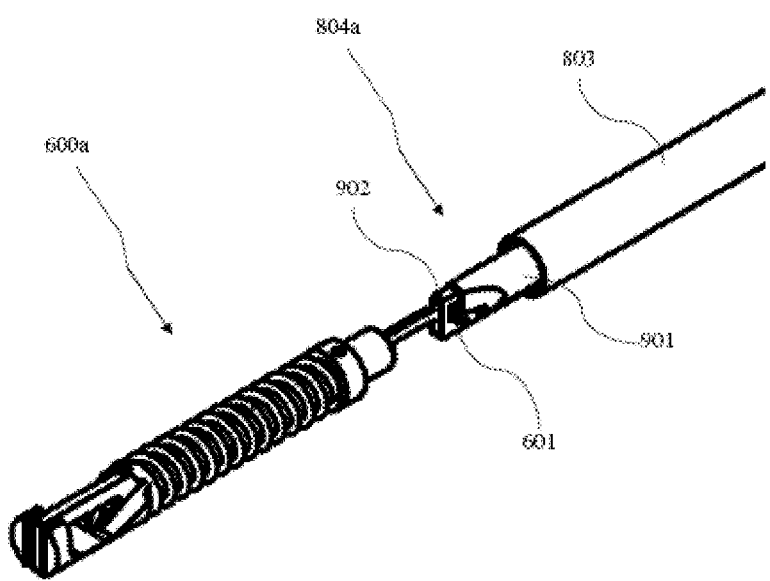
FIG. 9 is an enlarged view of FIG. 8, focused on the distal end of the introducer and the clip.
Figure 10:
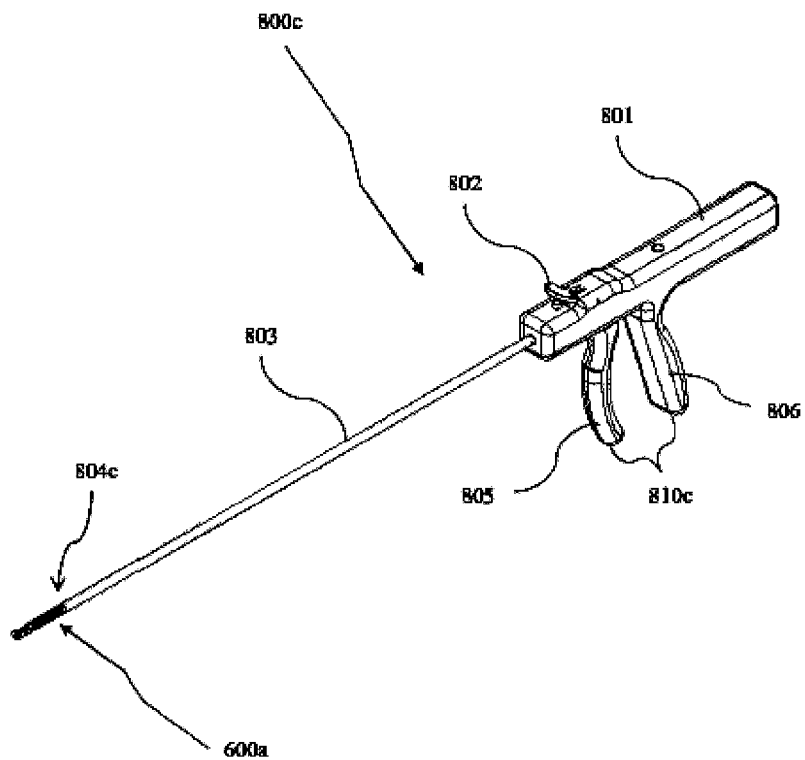
FIG. 10 is a perspective view of the introducer engaging the clip with the introducer's trigger almost fully contracted.
Figure 11:
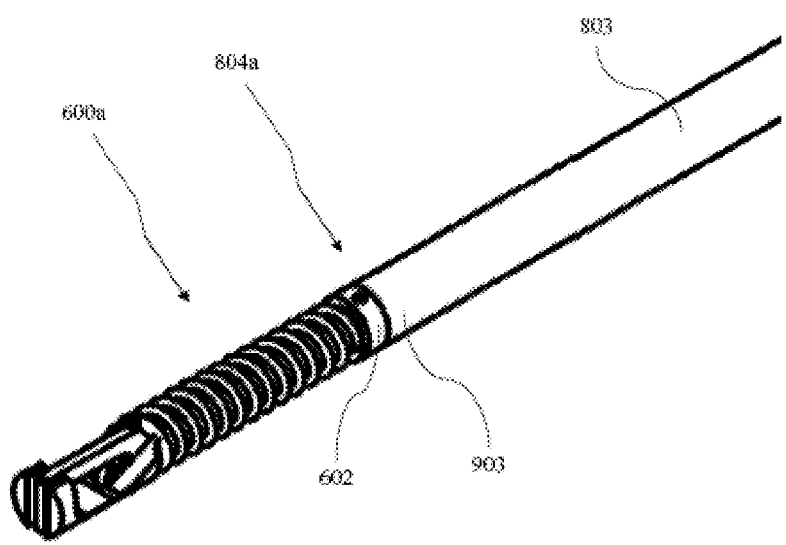
FIG. 11 is an enlarged view of FIG. 10, focused on the distal end of the introducer and the clip.
Figure 12:
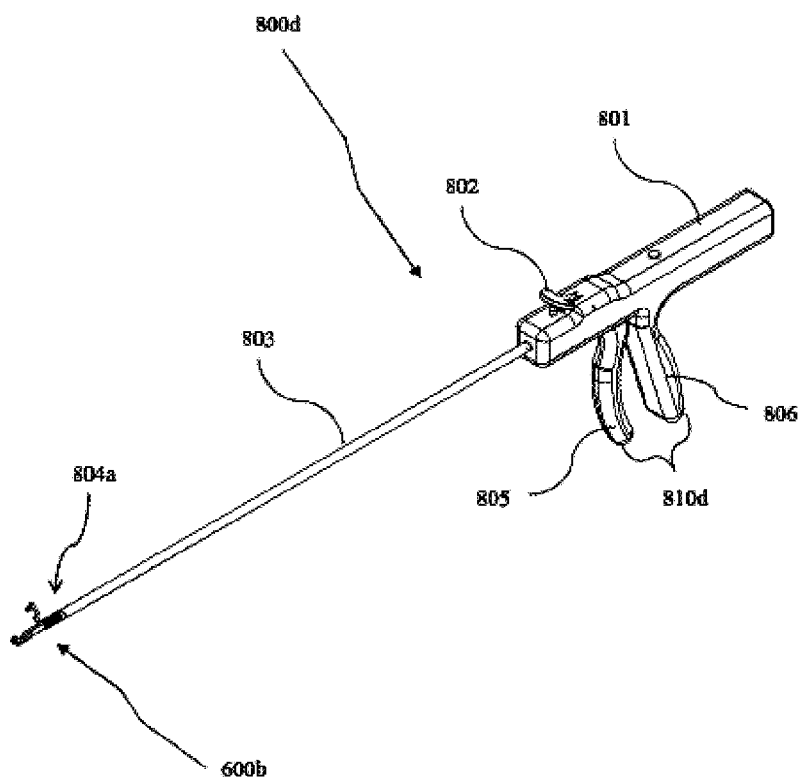
FIG. 12 is a perspective view of the introducer engaging the clip with the introducer's trigger fully contracted, the clip now in its open configuration.

Reference is made now to FIGS. 5-12 presenting an introducer 800(a-d) comprising a body 801 with a handle 806 for maneuvering the device, a trigger 805 and a stopper lever 802, a tubular shaft 803 with a distal engaging end 804(a-d). FIGS. 5-6 show the introducer 800a in its open position, engaging the hook 601 of a clip 600a by the introducer's hook 902. In this state, the trigger 805 and handle are 806 are at their largest separation 810a, such that the hook 902 is distally extended from the shaft 803 and "pusher" 901, and such that the clip 600a can be disconnect from the introducer. In FIG. 7 the body 801 of the introducer has been cross-sectioned so that the interior is shown. Within the body reside a piston 1002, a spring 1001 and through them runs a wire 1006 which is attached to the hook 902 near the distal end of the shaft 803. The piston 1002 has three grooves 1003, 1004, 1005 on which the stopper lever 802 can engage it and reversibly lock it in place. The trigger 805 is attached to the piston 1002 so that pulling the trigger proximally causes the piston to move proximally as well and compresses the spring 1001. Pressing the stopper lever 802 enables the spring 1001 to expand and moves the piston distally. In the open position described in FIGS. 5 and 6, the stopper lever engages the piston at the most proximal groove 1003. FIGS. 8 and 9 show the introducer 800b and clip 600a in partial contraction of the trigger 805, such that the stopper lever now engages the middle groove 1004. The separation between the trigger 805 and handle 806 is now smaller 810b. The hook 902 is now adjacent to the "pusher" 901 such that the hook 601 of the clip 600a is held in place. This configuration is typical for the manipulation of the clip once it has been attached to an organ or tissue between its jaws, allowing the anchoring and de-anchoring of the clip from the peritoneum. FIGS. 10 and 11 show the introducer 800c and clip 600a in nearly full contraction of the trigger 805, such that the stopper lever now engages the distal groove 1005. The separation between the trigger 805 and handle 806 is now very small 810c. The hook 902 and "pusher" 901 remain adjacent and are now concealed within the shaft 803. The ring 602 at proximal end of the body of the clip 600a is adjacent to the distal end of the shaft 903. This configuration is typical for the manipulation of the clip before it has been attached to an organ or tissue between its jaws, allowing the maneuvering of the device within the body cavity and insertion or removal from the cavity through a trocar. FIG. 12 shows the introducer 800d and clip 600b in complete contraction of the trigger 805. The separation between the trigger 805 and handle 806 is minimal 810d. The hook 902 of the introducer pulls on the hook 601 of the clip 600b as the body is held in place the contact of the proximal ring 602 and the distal end of the shaft 903. Thus the clip opens 600b and an organ or tissue can be engaged and caught between the jaws of the clip.

Figure 13:
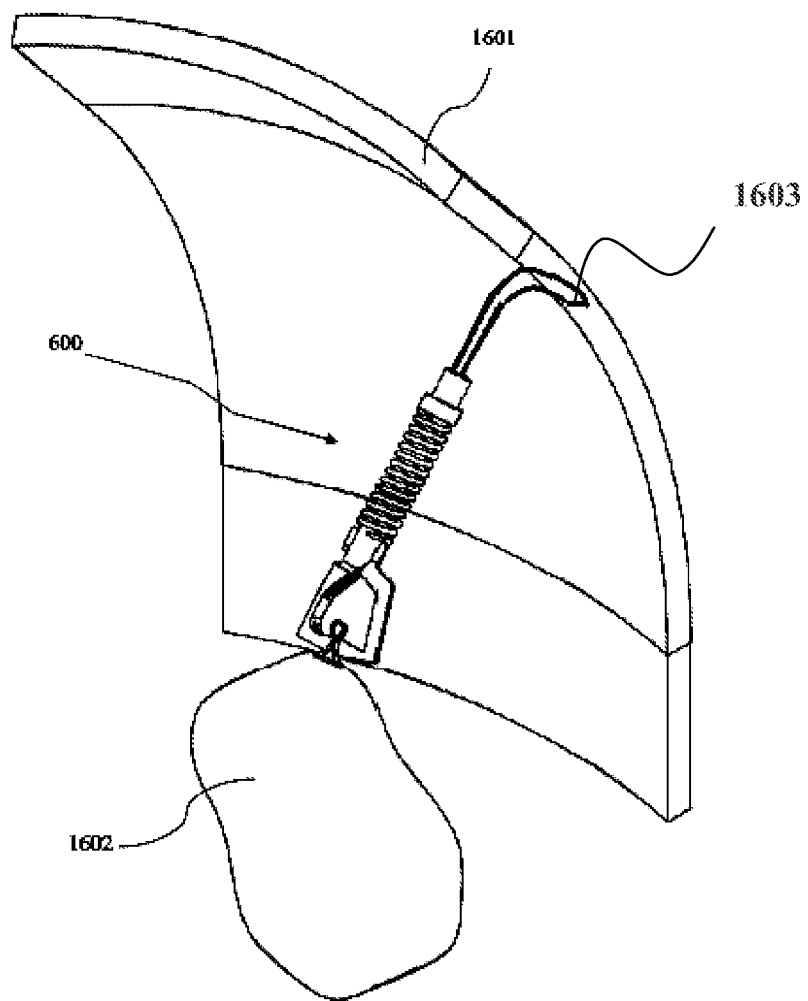
FIG. 13 is a perspective view of an example of use of the clip for retracting an organ and anchoring the clip on the peritoneum.
Figure 14:
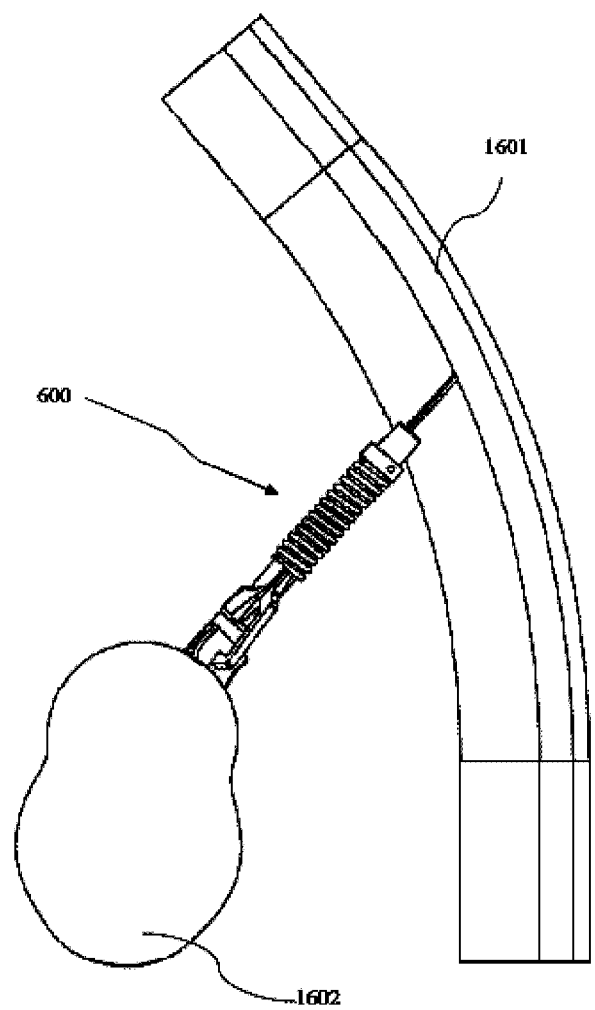
FIG. 14 is a side view of the same.
Figure 15:
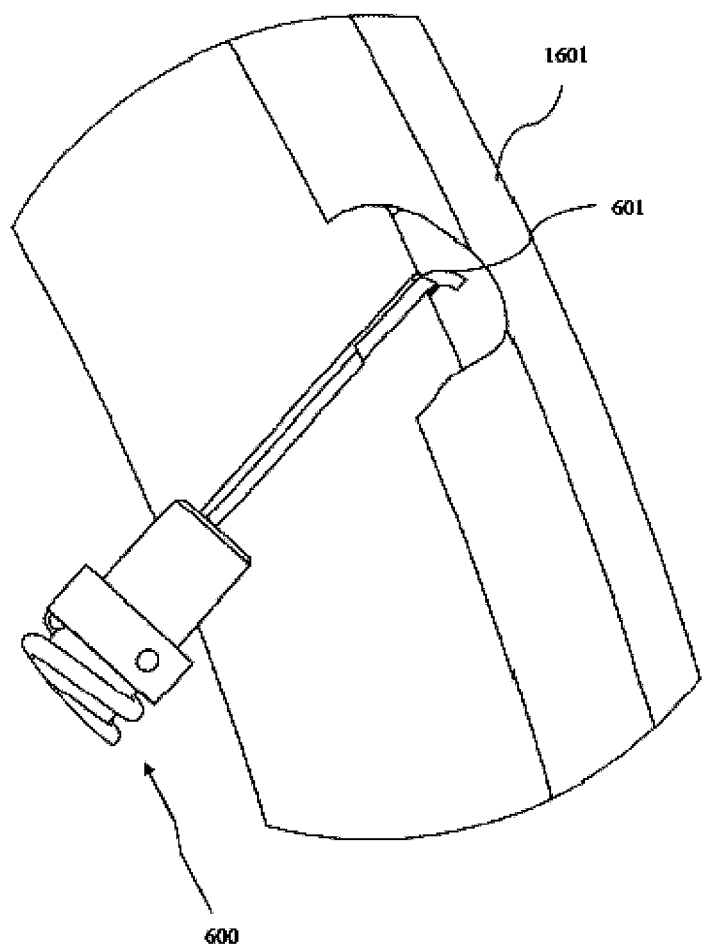
FIG. 15 is an enlarged cross sectional view of FIG. 14, focused on the hook of the clip anchored on the peritoneum.

Reference is made now to FIGS. 13-15, representing an example of application of the clip embodiment shown in FIGS. 3 and 4. A clip 600 is attached to an organ 1602 such that the jaws remain partially open, holding between them a tissue of the organ. As aforementioned, the partially compressed spring causes force to be applied between the jaws, holding the organ in place. At the other end, the hook 601 is attached to the internal abdominal wall 1601 by anchoring device 1603, such that the hook is piercing it and hangs from it, thus retracting the organ.

Figure 16:
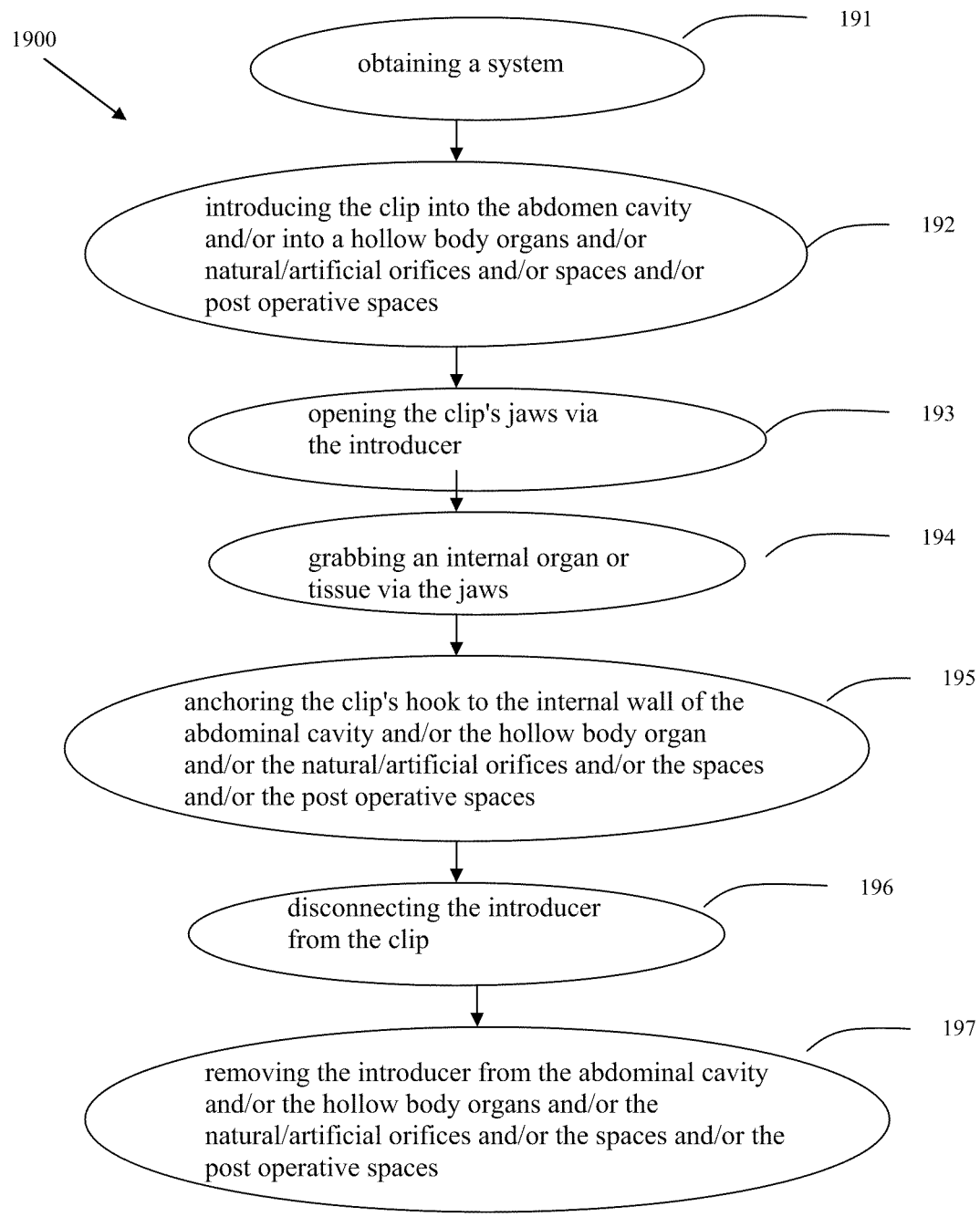
FIG. 16 schematically represents in a flow diagram, the method for retraction of an internal organ during a surgical procedure.

Reference is made now to FIG. 16 schematically represents in a flow diagram, the method (1900) for retraction of an internal organ during a surgical procedure. At the first step (191) a system is obtained. Next (192), the clip is introduced into the abdomen cavity and/or into a hollow body organs and/or natural/artificial orifices and/or spaces and/or post operative spaces. At the next step (193), the clip's jaws is opened via the introducer. At the final step (194), an internal organ or tissue is grabbed via the jaws. At the final step (195), the clip's hook is anchored to the internal wall of the abdominal cavity and/or the hollow body organ and/or the natural/ artificial orifices and/or the spaces and/or the post operative spaces. Next (196), the introducer is disconnected from the clip. Finally (197) the introducer is removed from the abdominal cavity and/or the hollow body organs and/or the natural/artificial orifices and/or the spaces and/or the post operative spaces.

EXAMPLE

A method of anchoring without using additional significant incisions to the abdominal wall using one clip:

In order to perform retraction of an internal organ during a minimally invasive procedure without the need of adding significant incisions to the abdominal wall or using another trocar and a dedicated resource that should hold the organ during the retraction time, the use of an introducer and clip of the present invention can be applied for instance:

Loading
1. Engage the hook 601 of the clip 600 with the hook 902 of the introducer 800.
2. Pull the Introducer trigger 805 and release it. The stopper mechanism will lock the trigger 805 in position, and the clip 600 will be loaded in the closed configuration at the end of the introducer tube 803. (As shown in FIG. 10).

Insertion
3. Insert the loaded introducer (FIG. 10) into the abdomen through a trocar in position on the abdominal wall.
4. When the desired organ for retraction is reached, pull the trigger 805 to open the clip's flap 607 (as shown in FIG. 12).

Retraction
5. Grab the organ 1602 between the teeth 606 and the flap 607 and release the trigger 802 to close the flap 607 on the organ.
6. Press once on the stopper 802 to release the clip 600 from the end of the introducer 800. The clip and introducer hooks 601 & 902 will still be engaged (as shown in FIG. 9).
7. Rotate the clip 600 so that the hook 601 is in the desired location on the internal abdominal wall 1601 for the specific procedure. Penetrate the abdominal tissue 1601 with the hook 601 to retract the organ 1602 (as shown in FIG. 13).

Introducer Removal
8. Press once on the stopper 802 to release the introducer hook 902, rotate the introducer 800 to disengage its hook 902 from the hook of the clip 601 and slide them apart with a lateral movement.
9. The introducer 800 may now be removed through the trocar, leaving the clip 600 in position.

Changing Retraction Position or Removing
10. Press once or twice on the stopper 802 of an empty introducer so that the hook 902 is extended
11. Introduce the empty introducer 800 through the trocar into the abdominal cavity.
12. Approaching from the side, engage the hook of the introducer 902 with the hook of the clip 601 and pull the trigger 805 until the stopper 802 clicks, fastening the hooks 601 & 902 together (as shown in FIG. 9).
13. With an upward motion of the introducer 800, remove the clip hook 601 from the tissue of the abdominal wall 1601.
14. You now have the following options:
a. Remove the clip:
Pull the trigger 805 until it clicks and opens the flap 607. Release the organ 1602 from the flap 607 and release the trigger 805 to close it and load the clip 600 into the introducer 800. Remove through the trocar.
b. Reposition the clip on the abdominal wall:
Follow steps 7-9.
c. Repeat the retraction procedure on a different organ or at a different position:
Follow steps 4-9.

The invention claimed is:

1. A clip for use during surgical procedures, said clip comprising:
a body (402, 602), comprising a distal end and a proximal end and characterized by a main longitudinal axis;
at least one shaft (408, 605) comprising a distal end and a proximal end and adapted to reciprocally move along said main longitudinal axis of said body;
at least one movable jaw (407, 607) pivotally connected to said body such that said movable jaw is configured to be reversibly transformable from at least one open configuration to at least one closed configuration;
at least one sleeve-like enveloping compression spring (403, 603) that at least partially encapsulates said at least one movable jaw and said body when said at least one movable jaw is in said closed configuration; and
an actuation engaging hook (401, 601) coupled to the proximal end of said shaft such that upon linear motion of said actuation engaging hook (401, 601), (i) said shaft is linearly moved toward one end of said body and (ii) said compression spring (403, 603) is compressed or released such that said at least one movable jaw (407, 607) is reconfigured;
wherein when said spring is released, said compression spring at least partially encapsulates said at least one movable jaw, thereby bringing said at least one movable jaw into said closed configuration, and further wherein when said at least one movable jaw is in said closed configuration, said clip has an essentially cylindrical profile and will fit within a standard 5 mm diameter trocar.

2. The clip according to claim 1, wherein said clip is characterized by a normally closed configuration and must be actuated in order to move said compression spring toward said proximal end, thereby causing said compression spring to cease encapsulating said at least one movable jaw and to transform said at least one movable jaw to said open configuration.

3. The clip according to claim 1, wherein said actuation engaging hook being of a shape and size appropriate for engagement within a body cavity or with another surgical instrument located within said body cavity.

4. The clip according to claim 3, wherein said actuation engaging hook is configured to anchor said clip to an internal surface of said body cavity.

5. The clip according to claim 3, wherein said surgical instrument is an introducer.

6. The use of the clip according to claim 1, wherein said surgical procedures is in performing an operation selected from the group consisting of anchoring minimally invasive surgical devices during said surgical procedures, retracting internal organs, retracting tissue within a body cavity, and temporarily holding a blood vessel.

7. The clip according to claim 1, wherein said transformation occurs without any plastic deformation of said at least one movable jaw (407, 607).

8. A system comprising:
a clip according to claim 1;
at least one anchoring device (1603) comprising at least partially reversible attachment means for attachment of said clip to an internal surface of a body cavity, said attachment means selected from the group consisting of vacuum means; magnetic means situated on at least one surface of said body cavity chosen from the group consisting of interior surfaces and exterior surfaces; mechanical means; adhesive means; and any combination thereof.

9. The system according to claim 8, wherein at least one condition chosen from the group consisting of:
said attachment means are vacuum means and comprise vacuum cups;
said attachment means are magnetic means chosen from the group consisting of magnets and electromagnets;

said attachment means are mechanical means chosen from the group consisting of barbs, fixation wires, and self-retaining clamps; and, said attachment means are adhesive means comprising pressure adhesive gel;

is true.

10. The clip according to claim 1, further comprising attaching means for at least partially reversibly attaching said clip to an internal surface of a body cavity.

11. The clip according to claim 10, wherein said attaching means are selected from the group consisting of magnets and electromagnets.

12. A method for retracting a first internal organ with respect to a second internal organ or the internal surface of a body cavity, during a surgical procedure that comprises a single incision; said method comprising:

obtaining a clip according to claim 1;

inserting said clip while said least one movable jaw (407, 607) is in said closed configuration;

reconfiguring said at least one movable jaw (407, 607) to said open configuration by:

linearly moving said actuation engaging hook (401,601) along said longitudinal axis of said clip towards said proximal end; and, compressing said compression spring (403,603);

grasping said first internal organ via said least one movable jaw (407, 607);

reconfiguring said at least one movable jaw (407, 607) to said closed configuration by:

linearly moving said actuation engaging hook (401,601) along said longitudinal axis of said clip towards said distal end; and, releasing said compression spring (403,603); and, anchoring said actuation engaging hook (401,601) to at least one location selected from said second internal organ and said internal surface of said body cavity; thereby retracting said first internal organ with respect to at least one location selected from the group consisting of said second internal organ and said internal surface of said body cavity.

13. The method according to claim 12, additionally comprising a step of repositioning said clip from a first position within body cavity to a second position within said body cavity.

14. The method according to claim 12, wherein said steps of reconfiguring said at least one movable jaw are performed without any plastic deformation to said at least one movable jaw (407, 607).

15. The method according to claim 12, additionally comprising a step of providing attaching means selected from the group consisting of vacuum means, magnets, electromagnets, mechanical means, adhesive means, and any combination thereof.

16. The clip according to claim 1, wherein linear movement of said compression spring results in radial movement of said at least one movable jaw.

17. The clip according to claim 1, wherein:

said sleeve-like enveloping compression spring partially encapsulates both said shaft and said body;

said actuation engaging hook (401, 601) is coupled to a stopping means (405) and to said at least one shaft (408, 605), said stopping means is configured to engage said sleeve-like enveloping compression spring and said at least one shaft is configured to engage said at least one movable jaw; and, an actuation of said clip is configured such that:

motion of said actuation engaging hook in a proximal direction along said longitudinal axis causes said stopping means to compress said spring and said at least one shaft to engage said at least one movable jaw thereby transforming said at least one movable jaw from said closed configuration to said open configuration; and, when said actuation engaging hook is released, said stopping means release said compression spring such that said compression spring expands to at least partially envelope said at least one movable jaw, thereby transforming said at least one movable jaw from said open configuration to said closed configuration.

\* \* \* \* \*